(12) United States Patent
Kulkarni et al.

(10) Patent No.: US 7,109,280 B2
(45) Date of Patent: *Sep. 19, 2006

(54) BLOCK COPOLYMERS AND PREPARATION THEREOF

(75) Inventors: Mohan Gopalkrishna Kulkarni, Pune (IN); Jayant Jagannath Khandare, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 52 days.

This patent is subject to a terminal disclaimer.

(21) Appl. No.: 10/697,181

(22) Filed: Oct. 29, 2003

(65) Prior Publication Data

US 2005/0095220 A1    May 5, 2005

(51) Int. Cl.
*C08F 218/00* (2006.01)

(52) U.S. Cl. .................. 526/234; 526/234; 526/238.2; 526/307.7; 526/309; 526/319; 526/328.5

(58) Field of Classification Search ................ 525/217, 525/218, 221, 228; 526/218.1, 238.2, 218.21, 526/234, 309, 319, 328.5, 307.7
See application file for complete search history.

(56) References Cited

U.S. PATENT DOCUMENTS

| | | | | |
|---|---|---|---|---|
| 5,587,442 A | * | 12/1996 | Kiessling et al. | 526/238.2 |
| 6,018,033 A | * | 1/2000 | Chen et al. | 536/4.1 |
| 6,043,328 A | * | 3/2000 | Domschke et al. | 526/279 |
| 6,187,762 B1 | * | 2/2001 | Mandeville et al. | 514/54 |
| 6,271,315 B1 | * | 8/2001 | Kiessling et al. | 525/326.1 |
| 6,316,606 B1 | * | 11/2001 | Kishi et al. | 536/4.1 |
| 6,512,109 B1 | * | 1/2003 | Nishimura | 536/123.1 |
| 6,538,072 B1 | * | 3/2003 | Kiessling et al. | 525/326.1 |
| 6,605,714 B1 | * | 8/2003 | Vaidya et al. | 536/55.2 |
| 6,630,154 B1 | * | 10/2003 | Fraker et al. | 424/423 |
| 6,660,484 B1 | * | 12/2003 | Charych et al. | 435/7.1 |
| 6,822,064 B1 | * | 11/2004 | Kulkarni et al. | 526/328.5 |

OTHER PUBLICATIONS

WO 2002/055021.*

* cited by examiner

*Primary Examiner*—David W. Wu
*Assistant Examiner*—M. Bernshteyn
(74) *Attorney, Agent, or Firm*—Merchant & Gould P.C.

(57) ABSTRACT

The present invention relates to block copolymers for applications in medicine and biotechnology and synthesis thereof. Block copolymers comprise polyvalent N-Acetyl Glucosamine (NAG) which bind more efficiently to lysozyme than NAG itself. The effective inhibition is possible even at very low ligand concentrations than reported earlier. The block copolymers could be used for prevention and treatment of bacterial and viral infections. Moreover these polymers can be stimuli sensitive and be used for the recovery of biomolecules. The methodology of preparation of block copolymers reported here can be extended to other polymers and ligands such as sialic acid and used for preventing influenza and/or rotavirus infections. It also provides a method for preparation of block copolymers wherein polymers comprising sequences of specific ligands are essential.

9 Claims, No Drawings

BLOCK COPOLYMERS AND PREPARATION THEREOF

FIELD OF INVENTION

This invention relates to block copolymers containing N-Acetyl Glucosamine (NAG) of molecular weight ranging from 1,000 Daltons to 2,00,000 Daltons having formula (1) herein below

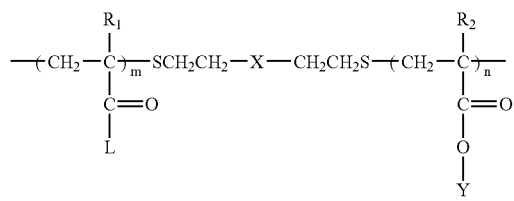

Formula (1)

wherein, $R_1$ is H, $CH_3$, $C_2H_5$, $C_6H_5$, $R_2$ is H, $CH_3$, $C_2H_5$, $C_6H_5$, X is an ester or an amide link, m is from 3 to 500, n is from 2 to 50, L is OH, $NH_2$, $OCH_3$, $NHCH(CH_3)_2$ Y may be N-Acetyl Glucosamine, mannose, galactose, sialic acid, fructose, ribulose, erythrolose, xylulose, psicose, sorbose, tagatose, glucopyranose, fructofuranose, deoxyribose, galactosamine, sucrose, lactose, isomaltose, maltose, cellobiose, cellulose and amylose.

More particularly it relates to the said block copolymers containing carbohydrate ligands and preparation thereof through the specific linkage mentioned herein. Still more particularly it relates to block copolymers which bind more strongly to lysozyme than NAG itself.

The block copolymers of the present invention as mentioned above are prepared by coupling oligoniers containing terminal reactive group of formula (2) claimed in our "Tri-block Copolymers and a Process for the Preparation of the Same' (Copending application No. 10/697,970) herein below with polymers containing terminal reactive group as given below (Formula 3)

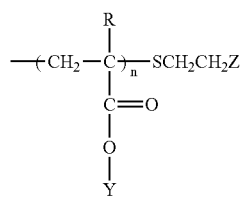

Formula (2)

wherein, R is H, $CH_3$, $C_2H_5$, $C_6H_5$, n is from 2 to 50, Z can be a OH or $NH_2$ group, Y may be N-Acetyl Glucosamine, mannose, galactose, sialic acid, fructose, ribulose, erytbrolose, xylulose, psicose, sorbose, tagatose, glucopyranose, fructofuranose, deoxyribose, galactosamine, sucrose, lactose, isomaltose, maltose, cellobiose, cellulose and amylose.

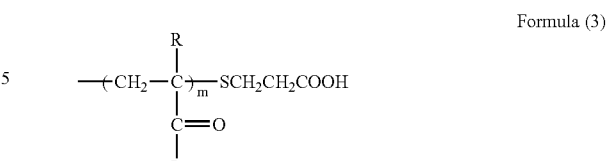

Formula (3)

wherein, R is H, $CH_3$, $C_2H_5$, $C_6H_5$, m is 3 to 500, L is OH, $NH_2$, $OCH_3$, $NHCH(CH_3)_2$ Block copolymers may be used for inhibition of viral infections and the recoveries of biomolecules. The approach of coupling two reactive polymers with polyvalent ligand N-Acetyl Glucosamine (NAG) is generic and can be used for other ligands such as sialic acid, galactose and mannose.

BACKGROUND OF THE INVENTION

Protein carbohydrates interactions play crucial role in biology for e.g. cell adhesion, cell recognition, immunoassay and fertilization. These biological events involve multivalent binding of the ligand to the host. The importance of carbohydrates in biologically relevant recognition processes has only recently come to light. (Feizi, et al., Biochem. J. 245:1, 1987; Belvilacqua, et al., Science 243:1160, 1989). They demonstrated carbohydrates, along with proteins and nucleic acids, act as primary biological information carriers.

Relatively few investigations are reported despite known role of carbohydrates in biology, for enhancing such interactions. Various targets for carbohydrate such as enzymes, proteins and viruses are being identified which can have numerous applications in therapeutics. Rouhi, A. M., (Chem. Engg. News, Sept. 23, 62–66, 1996) reported critical role of carbohydrates in various biological processes such as cell recognition, cell adhesion, cell differentiation, inflammation, viral and bacterial infection, tumerigenesis, and metastasis.

One of the major advantages of carbohydrate modification may be that it can impart change in physical characteristics such as solubility, stability, activity, antibody recognition and susceptibility to enzyme. Sharon, et al. (Science 246: 227–234, 1989) suggested carbohydrate portions of glycoconjugate molecules to be an important entity in biology.

Carbohydrates can be incorporated in polymer chain and utilized for binding to the receptors. Thereby, the polymers can be coupled with the other polymers containing ligands for multivalent effect.

Deng, S. J., and Narang, S. A. (Proc. Natl. Acad. Sci. USA, 92, 4992–4996, 1995) studied improved carbohydrate-binding single-chain antibodies from synthetic gene libraries. The dimeric antibodies have faster on-rates than the monomeric parent antibodies.

Stahl, et al. (U.S. Pat. No. 6,037,467, 2000) reported methods for preparing hydrophilic polymers by coupling the carbohydrate portion to the hydrophilic polymer portion.

Recent patent granted to Krepinsky, et al (U.S. Pat. No. 6,184,368, 2001) suggests the application of carbohydrates in preventing the infections. Mandeville, et al. (U.S. Pat. No. 5,891,862, 1999 and U.S. Pat. No. 6,187,762, 2001) reported the use of polyvalent polymers containing carbohydrates for the treatment of rotavirus infection.

There is a necessity to prepare multivalent ligands for enhanced binding as monovalent ligands display weak affinities and poor specificity towards the receptor binding sites. The resultant saccharide in a multivalent form can bind to the same substrate with greater affinity and specificity. The binding of cell surface receptors to multivalent carbohydrate molecules exhibits wide variety of biological responses and has unique edge over monovalent interactions (Mammen, et al. Angew. Chem., Int. Ed., 37, 2754–2794, 1998). Laura Kiessling and Nicola L. Pohl reported (Chemistry & Biology, 3:71–77, 1996) newer structural templates for the generation of multivalent carbohydrates containing multivalent saccharide derivatives useful for biological recognition events.

Synthetic multivalent moieties can be prepared with recognition of binding host sites, moreover they can be structured with molecular flexibility and orientation around the host. The characteristics of multivalent interactions are different than their monovalent counterparts as the latter involve one to one binding whereas multivalent interaction involves simultaneous binding of ligands at multiple sites of host molecules.

Many chemical and chemoenzymetic methods have been reported for the preparation of di- and trivalent ligands, dendrimers, and high molecular weight polymers, but involve complex synthetic methods. Thus, there is a need to devise simple methodology to obtain multivalent ligands of varying polymolecularity.

Polymers comprising multiple ligands could be more effective inhibitors for the host cell receptor, as a result of higher affinity for the pathogen. In addition, the higher molecular weight of the polymeric ligands also prevents the infection through steric exclusion. (Spaltenstein, A., and Whitesides, G. M., J. Am. Chem. Soc., 113, 686, 687, 1991).

Agglutination of erythrocytes caused by influenza virus can be prevented by use of polyvalent sialic acid inhibitors. This novel approach which is a model for pathogen-host interactions was reported by Mammen, M., and Whitesides, G., M., (J. Med. Chem. 38:21, 4179–90, 1995). The authors reported polymers containing sialic acid as effective inhibitors of influenza virus. Moreover, they suggested two favorable mechanisms for inhibition between the surfaces of virus and erythrocytes 1) High-affinity binding through polyvalency, and 2) Steric stabilization.

Sigal et al. (J. Am. Chem. Soc., 118:16, 3789–3800, 1996) studied the efficacy of polymers containing sialoside groups in inhibiting the adhesion of influenza virus to erythrocytes. They delineated the contributions of enhanced substrate ligand binding and steric considerations to efficiency of inhibition. These investigators reported sialic acid ligands, which can be exploited for the inhibition of the influenza virus. Monomeric inhibitor requires a higher concentration for inhibition since they are required to occupy at least half of the sialic acid binding sites on the virus, whereas the high molecular weight inhibitors need only a few attachments to achieve the same.

Dimick et al. (J. Am. Chem. Soc., Vol. 121 No 44, 10286, 1999) reported the molecular cluster glycoside effects and the synthesis of polyvalent ligands for the plant lectin concanavalin A.

Various methods have been reported in the past to synthesize multivalent ligands such as ring-opening metathesis polymerization (ROMP). ROMP has been used to generate well defined, biologically active polymers by Gibson et al., (Chem. Comm., 1095–1096, 1997) and Biagini et al., (Polymer, 39, 1007–1014, 1998).

A number of researchers have reported the synthesis and evaluation of sialoside-containing polyacrylamide inhibitors of the influenza virus. Whitesides and coworkers Mammen, M., Dahmann, G. & Whitesides, G. M. (J. Med. Chem. 38, 4179–4190, 1995) demonstrated effective inhibitors of hemagglutination by influenza virus synthesized from polymers comprising active ester groups. They used a broad range of sialic acid substituted acrylamide copolymers to probe the mechanism of inhibition of hemagglutination by multivalent carbohydrates.

Choi, S. K., Mammen, M. & Whitesides, G. M. (Chemistry & Biology, 3, 97–104, 1996) demonstrated the hemagglutination activity of monomeric sialic acid towards the influenza neuramimidase is considerably enhanced when the sialic acid is conjugated with a polymer so that it is presented as a multiple sialosides.

An understanding of the mode of action of the polyvalent sialosides provides a method for the design of inhibitors for influenza virus and insights into the mechanisms through which natural polyvalent ligands might act.

Carbohydrate-conjugated polymers have been based mostly on the polyacrylamide backbone. Alternative polymer in the backbone may be more effective. The effect of methods for synthesis of the saccharide-modified materials on their inhibition efficiency may be attributed to the density of functional groups.

Recently, the ring-opening metathesis polymerization (ROMP) methods have been applied for the synthesis of carbohydrate-substituted materials (Mortell, K. H., Gingras, M. & Kiessling, L. L. (J. Am. Chem. Soc. 116, 12053–12054, 1994). Like acrylamide polymerization, ROMP can be used in polar solvents and the carbohydrate residues need not be protected. Jason E. Gestwicki, Laura E. Strong, Christopher W. Cairo, L., Frederick J. Boehm, and Laura L. Kiessling, Chemistry & Biology, Vol. 9, 163–169, 2002, demonstrated the use of polymers generated by ring-opening metathesis polymerization (ROMP) as scaffolds to noncovalently assemble multiple copies of a lectin, the tetravalent protein concanavalin A (Con A).

The synergetic application of stimuli-responsive polymers and interactive molecules to form site-specific conjugates useful in variety of assays, separations, processing, and other uses are disclosed by Hoffman; Allan S.; Stayton; Patrick, S. (U.S. Pat. No. 5,998,588, 1999). The interactive molecules used can be biomolecules such as polysaccharides or glycoproteins, proteins or peptides, as antibodies, receptors, or enzymes, which specifically bind to ligands in the suitable environment. The inventors prepared stimuli-responsive polymers coupled to the recognition biomolecules at a specific site so that the polymer can be manipulated by stimulation to alter ligand-biomolecule binding at an adjacent binding site, for example, the biotin binding site of streptavidin, the antigen-binding site of an antibody or the active, substrate-binding site of an enzyme.

It is very important that ligand which is conjugated to polymers binds to active site of biomolecule must also be evicted from the binding site with change in environment. Such polymer conjugates find application in selective phase separation or affinity precipitation of biomolecules. The polymers used for such applications can be stimulus-responsive to an appropriate environmental stimulus.

Many chemical and chemoenzymatic routes of synthesizing multivalent ligands have been adapted for the preparation of di- and trivalent ligands, (Glick, G. D.; Toogood, P. L.; Wiley: D. C.; Skehel, J. J.; Knowles, J. R., J. Biol. Chem. 1991, 266, 23660–23669) dendrimers, and high molecular weight polymers, (Choi, S. K.; Mammen, M.; Whitesides, G. M. (J. Am. Chem. Soc., 119, 4103–4111, 1997) but well defined, linear oligomers synthesis in the past are complicated and requires multiple steps.

Thus, methods of synthesizing block copolymers with defined multivalent ligands for enhanced interactions provide a means for exploring biologically important processes.

Christopher W. Cairo, Jason E. Gestwicki, Motomu Kanai, and Laura L. Kiessling, J. Am. Chem. Soc. 124: 8,1614–1618, 2002) analyzed three aspects of receptor clustering: the stoichiometry of the complex, rate of cluster formation, and receptor proximity. Their experiments reveal that the density of binding sites on a multivalent ligand strongly influence binding characteristics. In general, high binding epitope density results in greater numbers of receptors bound per polymer, faster rates of clustering, and reduced inter-receptor distances. Ligands with low binding epitope density, are the most efficient on a binding epitope. Moreover, results provide insight into the design of ligands for controlling receptor-receptor interactions, which mimic mechanisms by which natural multivalent ligands bind to the substrates.

Damschroder et al. (U.S. Pat. No. 2,548,520, 1951) disclosed high molecular weight materials prepared by copolymerizing proteins conjugated with unsaturated monomers or proteins conjugated with preformed polymers. Synthesis of these high molecular weight materials generally requires temperatures up to 100° C. Such high temperatures are not well tolerated by most of the proteins. Thus the methods described are unsuitable for producing polymers of biologically active molecules.

Jaworek, et al. (U.S. Pat. No. 3,969,287, 1976) reports a method for the preparation of carrier-bound proteins, wherein the protein is reacted with a monomer containing at least one double bond capable of copolymerization. The carrier is provided as a water-insoluble solid or is produced in situ by the polymerization of water-soluble monomers in the presence of the protein monomer conjugate. The proteins utilized in the method of this invention are typically enzymes.

The carbohydrates such as NAG serve as ligands for lectins and lysozyme. Roy et al. (J. Chem. Soc. Chem. Comm., 1611–1613, 1992) reported custom designed glycopolymer synthesis by terpolymerizations. The N-acryloyl precursors and the acrylamide were used as effector molecules to provide specific properties such as hydrophobicity and mimicking tyrosine residues of proteins.

Mochalova et al. (Antiviral Research, 23,179–190, 1994) reported carbohydrate inhibitors like sialic acid anchored to polymeric or liposomal carriers. They conjugated glycylamido benzylsialoside with poly (acrylic acid-co-acrylamides) and dextrans. These polymeric ligands were evaluated for their ability to bind influenza A and B virus strains in cell culture.

Nishimura (Macromolecules 27, 4876–4880, 1994) demonstrated the inhibitory effect of glycosylated-cyclodextrins on the erythrocytes agglutination induced by wheat germ (*Triticum vulgaris*) agglutinin was observed at 240-fold lower concentration than its monomeric counterpart.

Dimick et al. (J. Am. Chem. Soc., 121, 44, 10286, 1999) explored newer strategies based on enhancing interactions. Synthesis of polyvalent ligands was reported and the role of glycosidic clusters in enhancing binding with plant lectin concanavalin A was demonstrated.

In an alternative approach Kanai, et al. (J. Am. Chem. Soc., 119, 9931–9932, 1997) reported ring opening metathesis polymerization (ROMP) consisting multivalent mannose binding to concanavalin A. However the methods are complicated and do not control "living" nature of glycopolymer.

Yamada et al. (Macromolecules, 32,3553–3558, 1999) reported controlled synthesis of amphiphilic block co polymers with pendant N-Acetyl Glucosamine (NAG) residues by living cationic polymerization. Copolymer architecture resulted in an enhancement in binding between Wheat Germ Agglutinin (WGA) and NAG.

Hoffman et al. (J. Biomater. Sci., Polym. Ed., 4:5, 545, 1993) synthesized carboxyl terminated poly (N-isopropyl acrylamide) oligomers, which were reacted with biopolymers to form thermo-reversible polymer-enzyme conjugates.

Krepinsky, et al. (U.S. Pat. No. 6,184,368, 2001) reported methods for synthesis of polyvalent carbohydrate molecules by glycosylations of partially protected polysaccharides bearing a single glycosylating agent or a mixture of glycosylating agents. The patent explains the non-productive binding of chitosan to lysozyme.

Chitosan (Formula 4) is linear, binary heteropolysaccharide and consists of 2-acetaamido-2-deoxy-β-D-glucose (GlcNAc; A-unit) and 2-amino-2-deoxy-β-D-glucose (GlcNAc, D-unit). The active site of lysozyme comprises subsites designated A–F. Specific binding of chitosan sequences to lysozyme begins with binding of the NAG units in the subsite C. Moreover natural ligands derived from glucose are susceptible to microbial growth. There is need to synthesize ligands similar to repeat units of chitosan which will not be hydrolyzed by lysozyme. These polymers are expected to be more stable than chitin and chitosan (Formula 4).

Formula (4)

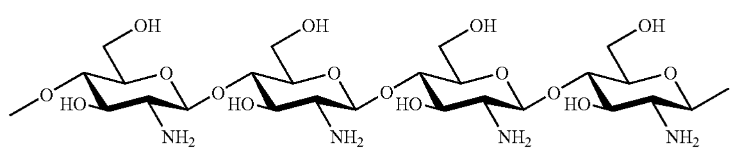

Chitosan

Apart from the type of the ligand, its distribution along the polymer chain also plays a crucial role in influencing the efficiency of the inhibition.

SUMMARY OF INVENTION

The present invention provides block copolymers for a biomolecular target and method for synthesis thereof. These block copolymers demonstrate selective binding to the target enzyme. The present invention also provides a method for obtaining affinity ligand useful for isolating biomolecule from a solution. The polymers reported here are AB block copolymers with suitable molecular weights which offer wide range of polymer architecture than those realized in the past. The molecular weight can be varied to the desired chain length for enhanced interactions. Moreover, block copolymers containing N-Acetyl Glucosamine reported here are easy to prepare and are resistant to enzyme degradation, reusable, stable and free from microbial contamination.

DETAILED DESCRIPTION OF THE INVENTION

The present invention relates to block copolymers containing carbohydrate ligands and preparation thereof. The polymers bearing terminal functional group are coupled with polymers containing functional polyvalent NAG.

The polymers comprising carbohydrate may also further be used in the treatment of bacterial or viral infections, and are expected not to cause drug resistance.

Block co polymers containing carbohydrate including NAG show enhanced hydrolytic stability and water solubility than natural polymers containing carbohydrate including NAG such as chitosan and chitin. They may be also used as anti-infective agents both for prevention and treatment of diseases, recovery of the naturally occurring as well as genetically manipulated biomolecules.

The approach described herein is a generic one and can be extended to other ligands as well. For example, sialic acid ligands are known to bind to influenza and rotavirus. Hence polymers comprising sialic acid can be expected to bind to these viruses and others containing similar receptor sites more strongly than the corresponding monomers, oligomers and macromers.

The enhanced interaction between the polymer conjugate with a specific binding site of biomolecule also finds applications in affinity separations, drug delivery and biotechnology.

To imitate and exploit this mechanism there is a need to devise a simple synthetic methodology, which will enhance substrate ligand interactions.

Design of high affinity protein carbohydrate binding systems can provide an alternative strategy for the treatment of infectious diseases e.g. influenza and rotavirus. This has the advantage as such agents will not have pathogen resistance to antibiotics and drugs. A new approach to treat influenza is based on the principle of inhibition of virus to the host cells. The inhibitors like sialic acid anchored to polymeric or liposomal carriers have been reported in the past.

The present invention involves coupling of NAG oligomers comprising terminal functional group adequately described and covered in our "Tri-block Copolymers and a Process for the Preparation of the Same," (Copending application Ser. No. 10/697,970) with polymers containing terminal reactive group. The block copolymerization of the oligomer with other polymer will always result in NAG sequences in juxtaposition with one another which will exhibit more pronounced inhibition than random polymers containing the same concentration of the ligand. The applicant have further demonstrated that block copolymers containing carbohydrate including NAG units as oligomers, bind to lysozyme more strongly as evidenced by values of $K_b$ and inhibit lysozyme more efficiently as evidenced by values of $I_{50}$. There is tremendous enhancement in interactions even the ligand concentration is very small, which indicates the steric stabilization effect.

Block copolymers of varied length and density will be useful for receptor ligand interactions of biological origin. Various chemical and chemoenzymatic methods have been reported in the past for the preparation of di- and trivalent ligands, dendrimers, and high molecular weight polymers but have proven to be complicated to synthesize.

Thus, there is necessity of a simple methodology to obtain block copolymers containing multivalent ligands of varying chain length.

The polyvalent interactions have several advantages over monovalent interactions as a result of mode of receptor binding. Moreover, multivalent interactions lead to conformational contact with biological receptors, which subsequently results in enhanced interaction.

Therefore, the objective of the present work is to synthesize block co polymers containing polyvalent ligand for enhanced interactions with the substrates.

In our "Tri-block Copolymers and a Process for the Preparation of the Same" (Copending application Ser. No. 10/697,970) the applicant have shown that the oligorners of NAG in which the NAG groups are juxtaposed to one another, bind more effectively to lysozyme as reflected in values of binding constant $(K_b)$ and the inhibition concentrations $I_{50}$. In the conventional technique of free radical copolymenization the distribution of moromers along the polymer chain depends upon the values of the monomer reactivity ratios which are determined primarily by the intrinsic structure of the monomer. Consequently the distribution of the NAG units in the copolymers comprising monomers bearing NAG cannot be tailored at will using conventional copolymerization techniques.

To overcome this problem the applicant have devised a novel strategy to ensure that the block copolymers prepared using conventional condensation polymerization technique which will always contain sequences of NAG units as desired.

The present invention provides block copolymers containing carbohydrate including NAG bearing oligomers for a biomolecular target and method for preparation thereof.

The approach described here is to prepare block copolymers containing polyvalent NAG ligands is simple and can be used to synthesize other polyvalent ligands such as sialic acid which bind to influenza virus and rotavirus. Such ligands may also be used as antiinfective agents both for prevention and treatment of diseases. Moreover, functional oligomeric NAG can be anchored to thermoprecipitating polymers that can be used for the recovery of biomolecules such as lysozyme and lectins.

The present invention relates to the block copolymers for application in the recovery of biomolecules.

The block copolymers comprising polyvalent ligands may further be used in the treatment of bacterial or viral infections, and are expected not to cause drug resistance.

The approach described herein is a generic one and can be extended to other systems as well for example sialic acid.

The present invention provides methods for the preparation for block copolymers containing N-Acetyl Glucosamine (NAG). Block copolymers provide improved binding and inhibition of biomolecules even at very low concentration. Moreover, these polymers being stimuli sensitive can be used for biomolecule recoveries. The method of preparation of block copolymers can be applied to other ligands such as sialic acid galactose and mannose.

The present invention relates to the block copolymers containing carbohydrate including NAG for applications in medicine and biotechnology.

It is possible to prepare either water-soluble or water-insoluble polymers by changing the chemical composition of the monomers, which may impart various chemical and physical-properties. e.g. water-soluble monomers such as N-isopropyl acrylamide (NIPA) may be homopolymerized to form water-soluble homopolymers.

Many polymers such as polysaccharides and polyacrylics which are water insoluble are being used in the biochemistry, affinity chromatography and immunoassays as solid-phase supports with passively adsorbed or covalently linked antibodies.

Various methods for the preparation of random, block or graft copolymers containing N-isopropyl acrylamide monomer are reported in the past. e.g. a number of monomers including butyl methacrylate, N-isopropyl methacrylamide and dextran sulfate have been polymerized with N-isopropyl acrylamide to prepare random copolymers.

A further aspect of the present invention is to prepare block copolymers comprising a polyvalent carbohydrate ligands.

Another aspect of the present invention is to use block copolymers containing carbohydrate including NAG for enhanced interactions with biomolecules.

The term "block copolymer" means any polymer prepared by coupling functional polyvalent polymers as AB block copolymer, using acrylic or methacrylic acid, acryloyl or methacryloyl chloride, glycidyl acrylate or methacrylate, glycerol acrylate or methacrylate, allyl chloride; hydroxy-lower-alkyl-acrylates, such as 2-hydroxyethyl methacrylate or 3-hydroxypropyl methacrylate, and amino-lower-alky-lacrylates, such as 2-amino-ethyl methacrylate coupled to polyvalent ligands such as NAG, sialic acid or mannose and may contain spacer arm. Polymers, which are soluble in water or water/polar organic solvent mixtures, are particularly preferred.

A "polyvalent ligand" means any polymer containing ligands N-Acetyl Glucosamine, mannose, galactose and sialic acid, fructose, ribulose, erythrolose, xylulose, psicose, sorbose, tagatose, glucopyranose, fructofuranose, deoxyribose, galactosamine, sucrose, lactose, isomaltose, maltose, cellobiose, cellulose and amylose. Polyvalent ligands are soluble in water or water/polar organic solvent mixtures are preferred.

A representative polyvalent ligand demonstrated here is poly.Acryloyl N-Acetyl Glucosamine (P.Ac.NAG) of formula (2) but does not limit the scope of the invention.

NAG is derived from chitosan which is a linear, binary heteropolysaccharide and consists 2-acetaamido-2-deoxy—β-D-glucose (GlcNAc; A-unit) and 2-amino 2-deoxy-β-D-glucose (GlcNAc, D-unit). Chitosan is a powerful natural ligand, which binds to lysozyme through the NAG residues. But it suffers from three major limitations) Chitosan is insoluble at neutral pH, which limits many applications. 2) Chitosan undergoes the transglycosylation and mutarotation, which substantially reduces its activity and efficiency 3) Chitosan is hydrolyzed by lysozyme.

The objective of the present invention is to provide a simple and novel process for the preparation of block copolymers comprising polyvalent NAG, which exhibit multivalent interactions. The merits of the approach have been highlighted using NAG as an illustration.

Another object of the present invention is to provide block copolymers containing carbohydrate including NAG which are more effective in binding with the lysozyme as evidenced by the values of the binding constants $K_b$ and relative inhibition of lysozyme more effectively as evaluated by the values of $I_{50}$.

Yet another object of the present invention is to provide block copolymers for applications in medicine and biotechnology.

Yet another object of the present invention is to provide a convenient method of preparation of polyvalent ligand NAG, mannose, galactose or sialic acid, fructose, ribulose, erythrolose, xylulose, psicose, sorbose, tagatose, glucopyranose, fructofuranose, deoxyribose, galactosamine, sucrose, lactose, isomaltose, maltose, cellobiose, cellulose and amylose.

Still another object of the present invention is to provide a convenient method of preparation block copolymers containing Acryloyl, Methacryloyl or Para Vinyl Benzoyl (PVB) moieties.

Yet another object of the present invention is to provide a convenient method of incorporation of polyvalent conjugates varying in molecular weights.

Yet another object of the present invention is to provide a convenient method of preparation of block copolymers of varying molecular weight and varying polyvalent ligands.

Yet another object is to provide a method of preparation of block copolymers containing carbohydrate including NAG ligands for enhanced interactions.

Still another object is to provide more stable ligands for the interactions with biomolecules than the natural polymers such as chitin and chitosan containing natural ligand NAG.

Accordingly the present invention provides a block copolymers having formula (1) and the molecular weight of the block copolymer ranging from 1,000 Daltons to 2,00,000 Daltons.

Formula (1)

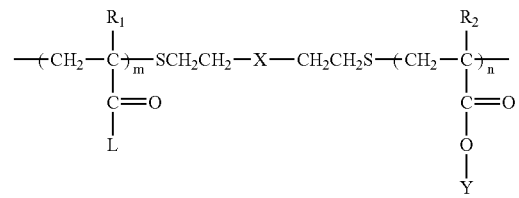

wherein,
$R_1$ is H, $CH_3$, $C_2H_5$, $C_6H_5$, $R_2$ is H, $CH_3$, $C_2H_5$, $C_6H_5$, X is an ester link or an amide link, m is from 3 to 500, n is from 2 to 50, L is OH, $NH_2$, $OCH_3$, $NHCH(CH_3)_2$ Y may be N-Acetyl Glucosamine, mannose, gal actose, sialic acid, fructose, ribulose, erythrolose, xylulose, psicose, sorbose, tagatose, glucopyranose, fructofuranose, deoxyribose, galactosamine, sucrose, lactose, isomaltose, maltose, cellobiose, cellulose and amylose.

The present invention also provides a simple and novel process for the preparation of block copolymers of formula 1, said process comprising:

i. dissolving the polymer containing terminal reactive group in a solvent, ii. adding to this a oligomer containing terminal reactive group, iii. dissolving a coupling agent to this reaction mixture, iv. allowing a reaction for a period of 24 hrs to 48 hrs at a room temperature in the range of 15 to 45° C., v. removing the unreacted coupling agent, and vi. precipitating in a non solvent and vacuum drying at room temperature in the range of 15 to 45° C. to obtain the block copolymer.

In another embodiment of the present invention the polymers containing terminal reactive group may be acrylic acid, methacrylic acid, methacryloyl chloride, acrylamide, N-isopropyl acrylamide (NIPA), 2-acrylamido-2-methyl propane-sulphonic acid (AMPS) methacrylate, acryloyl chloride, acryloyl morpholine, vinyl pyrrolidone, styrene, allyl alcohol and allyl amine.

In still another embodiment of the present invention, the polymer containing terminal reactive group ligands may be polymethacryloyl NAG or polyacryloyl NAG or Poly vinyl benzyl NAG.

In yet another embodiment of the present invention, the polymer containing terminal reactive group may contain COOH or OH groups at both ends.

In yet another embodiment of the present invention, the oligomer containing terminal reactive group ligands may be polymethacryloyl NAG or polyacryloyl NAG or Poly vinyl benzyl NAG.

In still another embodiment the oligomer containing terminal reactive group may contain COOH, OH or $NH_2$.

In still another embodiment the organic solvent used to dissolve the polymer containing terminal reactive group and oligomer containing terminal reactive group may be dimethyl formamide, tetra hydro furan or di-methyl sulfoxide.

In still another embodiment the coupling agent used may be selected from compounds such as Di Cyclohexyl Carbodiimide (DCC), 1-Cyclohexyl 3-(2-Morpholinoethyl) Carbodiimide metho-p-toluenesulfonate (CMC), 1-Ethyl-3-(3-Dimethylamino-propyl) Carbodiimide (EDC).

In yet another embodiment, the molar ratio of coupling agent for condensation of polymers may be 1:1.

In yet another embodiment, the non-solvent used to precipitate the block copolymers may be acetone, diethyl ether, hot water or hexane.

In yet another embodiment of the present invention the block copolymerization may be carried out at room temperature in the range of 15 to 45° C.

In a feature of the present invention, the block copolymers containing ligand may be useful for applications in medicine and biotechnology.

In yet another feature provides more stable block co polymers for the interactions with biomolecules than the natural polymers such as chitin and chitosan containing N-Acetyl Glucosamine.

In yet another feature of the present invention block copolymers containing polyvalent NAG are more efficient than copolymers of identical NAG content in the form of monomers, as evidenced by higher values of $K_b$ and lower values of $I_{50}$.

In yet another feature the present invention block copolymers containing ligands reported here can bind simultaneously on to the multiple sites of the enzyme/disease causing virus thereby enhancing the inhibitory effect.

In yet another feature of the present invention block copolymers containing polyvalent ligand provides greater accessibility to the ligand conjugate for binding with receptor biomolecule.

In yet another feature the method used for estimation of the relative inhibition may be in terms of $I_{50}$ mM and $I_{max}$ mM values.

In yet another feature of the present invention block copolymers containing ligands reported herein are effective at very low concentration, which is advantage when the ligand under consideration are expensive e.g. sialic acid.

In yet another feature of the present invention, block copolymers containing ligands reported here containing carbohydrate including NAG are stable, water soluble, resistant to degradation, and free from microbial contamination which is an advantage over the natural polymers such as chitin and chitosan.

It is also expected that the presence of multiple ligands in the polymer backbone will enhance binding to the virus and biomolecules such as influenza virus, rotavirus, wheat germ agglutinin. The block copolymers containing multiple ligands can potentially interact with multiple receptors simultaneously thereby enhancing the binding to lysozyme.

Previous methods of synthesis of copolymers and block co polymers are complicated, moreover there are few reports available on method of incorporation of polyvalent ligands in such block copolymers.

It is also reported that the polymeric fucosides are resistant to neuramimidase enzyme present on the surface of influenza virus. The viruses cleave sialic acid groups from molecules that bind to the surface of the virus, and thereby destroy the binding ability.

The block copolymers reported here may need lower incorporation of polyvalent ligand than reported in the past. Moreover, they are effective at very low concentration, which is a significant advantage when the ligands under consideration are expensive e.g. sialic acid. The process reported here for the incorporation of polyvalent ligands into polymerizable macromers is relatively simple and involves lesser steps.

The ability of block copolymers to bind virus and biomolecules provides a means of developing new therapeutic agents. These polymers can be used in various applications such as affinity separations and immunoassays.

The block copolymers are of suitable molecular weights, which can efficiently bind to the target site.

The ligands on block copolymers have ability to bind to various substrate molecules simultaneously. It is expected that the presence of multiple ligands in the backbone can enhance binding to the viruses and biomolecules.

The efficiency of ligand binding with the specific substrates/receptors can be quantified in various terms such as binding constants ($K_b$) and the relative inhibition ($I_{50}$) in presence of the substrates.

The process for the preparation of the block copolymers of the present invention is described herein below with reference to examples which are illustrative only and should not be construed to limit the scope of the present invention in any manner whatsoever.

EXAMPLE 1

This example describes the process for the preparation of P(N-Iso Propyl Acrylamide (PNIPA) bearing terminal COOH functional groups.

2.2 gm. N-Iso Propyl Acrylamide (0.0194 M) and 0.000776 M (0.082346 ml) Mercapto Propionic Acid (MPA) as a chain transfer agent was dissolved in iso-butyl alcohol (25 ml) in a round bottom flask. The mixture was stirred under nitrogen purging to obtain a clear solution. The polymerization was carried out at 60° C. for 24 hrs using 2,2'-Azo Bis Iso Butyro Nitrile (AIBN) as initiator. The AIBN concentration was varied so as to obtain polymers of different molecular weights containing carboxyl end groups. The polymer obtained was cooled at room temperature and precipitated into diethyl ether. The polymer was dried under vacuum for 24 hrs. Molecular Weights of PNIPA was determined using Vapor Phase Osmometer (Table 1).

EXAMPLE 2

This example describes the process for the preparation of block copolymers of P (N-Iso Propyl Acrylamide bearing terminal carboxyl group (P. NIPA. COOH) with Poly Acryloyl N-Acetyl Glucosamine bearing terminal hydroxyl group (P.Ac.NAG.OH).

1 gm. of carboxyl terminated Poly. N-Iso Propyl Acrylamide (P. NIPA. COOH) and 0.47 gm of hydroxyl terminated Poly Acryloyl N-Acetyl Glucosamine (P.Ac.NAG.OH) were dissolved in 25 ml DMF to obtain a clear solution. 0.16 gm of Di Cyclohexyl Carbodiimide (DCC) was added at room temperature and the reaction was carried out for 24 hrs at room tempearture. Di Cyclohexyl Urea (DCU) was filtered off. The polymer was precipitated in diethyl ether and reprecipitated and dried under vacuum at room temperature.

EXAMPLE 3

This example describes estimation of binding constant ($K_b$) of block copolymers containing carbohydrate including NAG by fluorescence spectrophotometric method and the enhancement resulting from conjugation with monomers and monomer containing spacer.

Fluorescence spectra of lysozyme were recorded on a Perkin Elmer LS-50 B luminescence spectrophotometer. Excitation frequency was 285 nm. Solutions of lysozyme and N-Acetyl Glucosamine were prepared in 0.066 M phosphate buffer pH 6.2, containing 0.0154 M sodium chloride and 0.008 M sodium azide. 0.1 milliliter of lysozyme 80 µg/ml was mixed with solution containing different ligand concentration in a 2 ml capacity 10 mm square quartz cells maintained at 18° C. Phosphate buffer was added to make the volume to 2 ml. The fluorescence intensities of the solutions were measured, relative to the solutions containing enzymes and buffer mixtures of the identical concentration reference. The relative fluorescence intensity of lysozyme saturated with solution containing different ligand concentration, $F\infty$, was extrapolated from the experimental values by plotting $1/(F_O-F)$ against $1/[S]$ where F is the measured fluorescence of a solution containing enzyme with given substrate concentration [S] and $F_O$ is the fluorescence of a solution of enzyme alone (Chipman et al., J. Biol. Chem., 242–19, 4388–4394, 1967). The highest concentration of polymer substrates was used when enzyme was saturated more than 85%.

TABLE 1

Binding Constants for AB Block Copolymers Containing NAG

| Mole % NAG | Mole A | Moles B | Mol. Wt. A | Mol. Wt B | $K_b$ | LCST |
|---|---|---|---|---|---|---|
| 16.09 | 53.02 | 10.17 | 6000 | 2808 | $4.20 \times 10^5$ | 34.5 |
| 11.91 | 70.67 | 9.56 | 8000 | 2631 | $2.05 \times 10^5$ | 34.5 |
| 4.19 | 53.02 | 2.32 | 6000 | 638 | $6.30 \times 10^5$ | 34.5 |
| 3.17 | 70.67 | 2.32 | 8000 | 638 | $1.00 \times 10^6$ | 34.5 |
| 8.04 | 26.51 | 2.32 | 3000 | 638 | $5.01 \times 10^5$ | 34.5 |
| 1.84 | 123.7 | 2.32 | 14000 | 638 | $1.38 \times 10^6$ | 34.5 |
| 3.72 | 123.7 | 4.78 | 14000 | 1315 | $6.40 \times 10^5$ | 34.5 |
| 7.17 | 123.7 | 9.56 | 14000 | 2631 | $1.26 \times 10^6$ | 34.5 |
| 9.76 | 88.37 | 9.56 | 10000 | 2631 | $8.37 \times 10^5$ | 34.5 |
| 15.59 | 53.02 | 9.56 | 6000 | 2631 | $6.30 \times 10^5$ | 34.5 |
| 26.5 | 26.51 | 9.56 | 3000 | 2631 | $3.20 \times 10^5$ | 34.5 |

Binding constants for AB diblock copolymers are summarized in Table 1 wherein, block copolymer of molecular weight 14000–638 has binding constant $1.38 \times 10^6$ which shows 38000 folds enhancement over NAG ($5.24 \times 10^2$).

EXAMPLE 4

Estimation of binding of lysozyme by block copolymers containing carbohydrate including NAG.

Relative binding of block copolymers containing carbohydrate including NAG was estimated by using a procedure reported by Neuberger and Wilson (1967) 1.5% w/v stock solutions of polymeric ligands was prepared in 0.0066 M phosphate buffer pH 6.2 containing 0.0154 m sodium chloride and 0.008 M sodium azide. One milliliter of stock solution containing different block copolymer ligand concentration was mixed with 1.6 ml of 78 µg/ml of *Micrococcus lysodeikticus* in a 3-ml capacity glass cuvette. The mixture was incubated for 5 minutes at 20° C. To this mixture 0.1 ml of lysozyme (27 µg/ml) was added and mixed thoroughly. The absorbance at 450 nm ($\Delta_{A450}$) was recorded for 30 seconds. A blank reading without the polymer ligand was noted and the change in the absorbance per second was calculated. Then relative inhibition was calculated.

TABLE 2

Estimation of Relative Inhibition of Lysozyme by AB Block Copolymers Containing NAG

| Mole % NAG | Mole A | Moles B | Mol. Wt A | Mol. Wt. B | $I_{50}$ mM | $I_{max}$ | $I_{max}$ mM |
|---|---|---|---|---|---|---|---|
| 16.09 | 53.02 | 10.17 | 6000 | 2808 | 0.00737 | 67.05 | 0.0064 |
| 11.91 | 70.67 | 9.56 | 8000 | 2631 | 0.00349 | 71.17 | 0.0049 |
| 4.19 | 53.02 | 2.32 | 6000 | 638 | 0.00076 | 68 | 0.0015 |
| 3.17 | 70.67 | 2.32 | 8000 | 638 | 0.00075 | 70.02 | 0.0014 |
| 8.04 | 26.51 | 2.32 | 3000 | 638 | 0.00241 | 67.25 | 0.0035 |
| 1.84 | 123.7 | 2.32 | 14000 | 638 | 0.00026 | 94.30 | 0.0006 |
| 3.72 | 123.7 | 4.78 | 14000 | 1315 | 0.00069 | 74.22 | 0.0015 |
| 7.17 | 123.7 | 9.56 | 14000 | 2631 | 0.00159 | 73.80 | 0.00287 |
| 9.76 | 88.37 | 9.56 | 10000 | 2631 | 0.00210 | 75.9 | 0.0037 |
| 15.59 | 53.02 | 9.56 | 6000 | 2631 | 0.0029 | 69.22 | 0.0069 |
| 26.5 | 26.51 | 956 | 3000 | 2631 | 0.0038 | 61.83 | 0.0075 |

The relative inhibition of lysozyme in terms of 150 for monomer NAG is 74.00 mM and has decreased to 0.00026 mM, which is almost 290000 times lower than that for NAG.

The $I_{max}$ have increased from 55.29 mM to 94.30%.

Block copolymers sequences follow one another along the main polymer chain. The various possibilities of sequence of the polymer chain in block copolymers are known in the art. A person skilled in the art can easily design the various possible sequences on the basis of aforementioned information.

The Advantages of the Present Invention Are As Follows:
1. The block copolymers reported here comprise polyvalent ligands for enhanced interactions.
2. The block copolymers have higher molecular weight and demonstrate greater efficiency through steric exclusion.
3. The block copolymers have greater water solubility, stability, and susceptibility to enzyme from hydrolysis.
4. The enhancement in binding due to polyvalent interactions arises from the conformational flexibility of copolymers with the biological receptors.
5. The method of preparation of block copolymers containing polyvalent ligands is convenient and simple.
6. The block copolymers containing polyvalent NAG are effective even at low ligand concentration than monomer itself.
7. The block copolymers are thermoprecipitating polymers and make them suitable for biomolecule recovery.
8. The block copolymers can bind simultaneously to multiple binding sites of biomolecules thereby exhibiting enhanced interactions.
9. The methodology of preparation of block copolymers reported here can be extended to other polymers and ligands such as sialic acid and used for preventing influenza and/or rotavirus infections.

10. A method of preparation of block copolymers reported here comprises sequences of specific ligands.

The invention claimed is:

1. Block copolymers having formula 1:

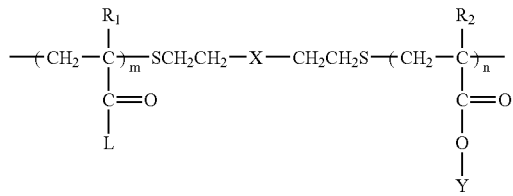

Wherein,
$R_1$ is H, $CH_3$, $C_2H_5$, $C_6H_5$,
$R_2$ is H, $CH_3$, $C_2H_5$, $C_6H_5$,
X is an ester or amide link,
m is in the range of 3 to 500,
n is in the range of 2 to 50,
L is OH, $NH_2$, $OCH_3$, $NHCH(CH_3)_2$,
Y is N-Acetyl Glucosamine, mannose, galactose, sialic acid, fructose, ribulose, erythrolose, xylulose, psicose, sorbose, tagatose, glucopyransoe, fructofuranose, deoxyribose, galactosamine, sucrose, lactose, isomaltose, maltose, cellobiose, cellulose and amylose.

2. Block copolymers as claimed in claim 1, wherein weight average molecular weight of block copolymers is in the range of 1000 Daltons to 200000 Daltons.

3. Block copolymers as claimed in claim 1, wherein the block copolymers are more stable for interactions with bio-molecules than the natural polymers such as chitin and chitosan having natural N-Acetyl glucosamine.

4. Block copolymers as claimed in claim 1, wherein the block copolymers having ligands enhances binding effect by binding simultaneously on the multiple sites of the enzyme/disease causing viruses.

5. Block copolymers as claimed in claim 1, wherein the block copolymers provide greater accessibility to the ligand conjugate for binding with receptor bio-molecules.

6. Block copolymers as claimed in claim 1, wherein block copolymers having ligands and NAG are stable, water soluble, resistant to degradation and free from the microbial contamination thus having advantage over natural polymers like chitin and chitosan.

7. Block copolymers as claimed in claim 1, wherein different monomers are incorporated in the block copolymer chain to make it hydrophobic or hydrophilic.

8. Block copolymer as claimed in claim 1, wherein the copolymer has an $I_{50}$ for inhibition of lysozyme of 0.00026 mM compared with monomer NAG having an $I_{50}$ of 74 mM.

9. Block copolymer as claimed in claim 1, wherein the copolymer has weight-average molecular weight 14,000 and binding constant $1.38 \times 10^6$, which shows 30,000 folds enhancement over NAG ($5.24 \times 10^2$).

* * * * *